US008865202B2

(12) United States Patent
Zerbe et al.

(10) Patent No.: US 8,865,202 B2
(45) Date of Patent: *Oct. 21, 2014

(54) WATER SOLUBLE FILM FOR ORAL ADMINISTRATION WITH INSTANT WETTABILITY

(75) Inventors: Horst Georg Zerbe, Green Pond, NJ (US); Jian-Hwa Guo, Sparta, NJ (US); Anthony Serino, Boonton, NJ (US)

(73) Assignee: LTS LOHMANN Therapie-Systeme AG, Andernach (DE)

( * ) Notice: Subject to any disclaimer, the term of this patent is extended or adjusted under 35 U.S.C. 154(b) by 936 days.

This patent is subject to a terminal disclaimer.

(21) Appl. No.: 10/771,388

(22) Filed: Feb. 5, 2004

(65) Prior Publication Data
US 2004/0156885 A1 Aug. 12, 2004

Related U.S. Application Data

(60) Continuation of application No. 10/143,962, filed on May 14, 2002, now Pat. No. 6,709,671, which is a continuation of application No. 09/927,327, filed on Aug. 13, 2001, now abandoned, which is a continuation of application No. 09/630,562, filed on Aug. 2, 2000, now Pat. No. 6,284,264, which is a division of application No. 09/287,181, filed on Apr. 6, 1999, now Pat. No. 6,177,096, which is a continuation of application No. 08/904,607, filed on Aug. 1, 1997, now Pat. No. 5,948,430.

(30) Foreign Application Priority Data

Nov. 11, 1996 (DE) .................................. 196 46 392

(51) Int. Cl.
*A61K 8/73* (2006.01)
*A61K 8/72* (2006.01)
*A61K 47/00* (2006.01)
*A61K 47/38* (2006.01)
*A61Q 11/00* (2006.01)
*A61K 31/44* (2006.01)
*A61K 8/02* (2006.01)
*A61K 9/00* (2006.01)
*A61K 8/39* (2006.01)
*A61K 8/81* (2006.01)
*A61K 8/92* (2006.01)
*A61K 8/90* (2006.01)
*A61K 8/49* (2006.01)

(52) U.S. Cl.
CPC ............... *A61K 8/0208* (2013.01); *A61K 9/006* (2013.01); *A61K 8/39* (2013.01); *A61K 8/8176* (2013.01); *A61K 8/922* (2013.01); *A61K 8/90* (2013.01); *A61Q 11/00* (2013.01); *A61K 8/4926* (2013.01); *A61K 8/731* (2013.01)
USPC ........... 424/435; 424/401; 424/439; 424/434; 131/270

(58) Field of Classification Search
USPC .................. 424/435, 434, 401, 439; 131/270
See application file for complete search history.

(56) References Cited

U.S. PATENT DOCUMENTS

| 3,931,824 | A | * | 1/1976 | Miano et al. .................. 131/359 |
|---|---|---|---|---|
| 4,029,757 | A | | 6/1977 | Mlodozeniec et al. |
| 4,029,758 | A | | 6/1977 | Mlodozeniec et al. |
| 4,031,200 | A | | 6/1977 | Reif |
| 4,076,856 | A | * | 2/1978 | Zeitlin et al. .................. 426/594 |
| 4,082,841 | A | * | 4/1978 | Pader ............................. 424/50 |
| 4,579,858 | A | | 4/1986 | Ferno et al. |
| 4,713,239 | A | | 12/1987 | Babaian et al. |
| 4,764,378 | A | * | 8/1988 | Keith et al. .................... 424/435 |
| 4,772,470 | A | * | 9/1988 | Inoue et al. .................... 424/435 |
| 4,786,505 | A | * | 11/1988 | Lovgren et al. ............... 424/468 |
| 4,855,142 | A | * | 8/1989 | Fankhauser et al. .......... 424/434 |
| 4,876,092 | A | | 10/1989 | Mizobuchi et al. |
| 4,900,552 | A | | 2/1990 | Sanvordeker et al. |
| 4,944,949 | A | * | 7/1990 | Story et al. .................... 424/451 |
| 5,047,244 | A | | 9/1991 | Sanvordeker et al. |
| 5,147,654 | A | | 9/1992 | Place et al. |
| 5,229,164 | A | | 7/1993 | Pins et al. |
| 5,288,497 | A | * | 2/1994 | Stanley et al. ................. 424/440 |
| 5,328,682 | A | * | 7/1994 | Pullen et al. ................... 424/49 |
| 5,346,701 | A | | 9/1994 | Heiber et al. |
| 5,354,551 | A | * | 10/1994 | Schmidt ......................... 424/49 |
| 5,413,792 | A | | 5/1995 | Ninomiya et al. |
| 5,414,005 | A | | 5/1995 | Schneider et al. |

(Continued)

FOREIGN PATENT DOCUMENTS

| CA | 1 263 312 | 11/1989 |
|---|---|---|
| DE | 24 32 925 | 1/1976 |

(Continued)

OTHER PUBLICATIONS

Patent Abstracts of Japan for JP 58-059910, published Apr. 9, 1983.
Patent Abstracts of Japan for JP 03-246220, published Nov. 1, 1991.
Patent Abstracts of Japan for JP 03-209327, published Sep. 12, 1991.
Patent Abstracts of Japan for JP 03-209326, published Sep. 12, 1991.
Patent Abstracts of Japan for JP 63-310818, published Dec. 19, 1988.
Patent Abstracts of Japan for JP 62-135417, published Jun. 18, 1987.
F.V. Bruchhausen (ed.): Hagers Handbuch der pharmazeutischen Praxis, vol. 2, 1991, p. 849 (in German) & and partial English translation thereof.

(Continued)

Primary Examiner — Lezah Roberts
(74) Attorney, Agent, or Firm — Wenderoth, Lind & Ponack, L.L.P.

(57) ABSTRACT

A composition containing therapeutic agents and/or breath freshening agents for use in the oral cavity is disclosed. The carrier comprises water-soluble polymers in combination with certain ingredients and provides a therapeutic and/or cosmetic effect. The film is coated and dried utilizing existing coating technology and exhibits instant wettability followed by rapid dissolution/disintegration upon administration in the oral cavity.

19 Claims, No Drawings

(56) References Cited

U.S. PATENT DOCUMENTS

| | | | |
|---|---|---|---|
| 5,446,070 A | | 8/1995 | Mantelle |
| 5,456,745 A | * | 10/1995 | Roreger et al. ............ 106/140.1 |
| 5,462,749 A | | 10/1995 | Rencher |
| 5,472,704 A | | 12/1995 | Santus et al. |
| 5,492,937 A | | 2/1996 | Bogentoft et al. |
| 5,565,466 A | | 10/1996 | Gioco et al. |
| 5,599,554 A | | 2/1997 | Majeti |
| 5,626,866 A | | 5/1997 | Ebert et al. |
| 5,629,003 A | | 5/1997 | Horstmann et al. |
| 5,686,094 A | * | 11/1997 | Acharya ...................... 424/434 |
| 5,700,478 A | | 12/1997 | Biegajski et al. |
| 5,733,574 A | * | 3/1998 | Dam ............................ 424/464 |
| 5,783,207 A | * | 7/1998 | Stanley et al. ............... 424/440 |
| 5,785,989 A | | 7/1998 | Stanley et al. |
| 5,804,209 A | | 9/1998 | De Ponti et al. |
| 5,824,334 A | | 10/1998 | Stanley et al. |
| 5,853,740 A | | 12/1998 | Lu et al. |
| 5,871,905 A | | 2/1999 | Thieme et al. |
| 5,952,382 A | | 9/1999 | Bernardon |
| 5,955,098 A | | 9/1999 | Dugger, III |
| 6,165,512 A | * | 12/2000 | Mezaache et al. ............ 424/489 |
| 6,221,383 B1 | | 4/2001 | Miranda et al. |
| 6,264,981 B1 | | 7/2001 | Zhang et al. |
| 6,335,023 B1 | | 1/2002 | Yu et al. |
| 6,342,496 B1 | | 1/2002 | Jerussi et al. |
| 6,436,407 B1 | | 8/2002 | Clements et al. |
| 6,489,341 B1 | | 12/2002 | Jerussi |
| 6,552,024 B1 | | 4/2003 | Chen et al. |
| 6,592,887 B2 | | 7/2003 | Zerbe et al. |
| 2003/0099690 A1 | | 5/2003 | Awamura et al. |
| 2003/0118653 A1 | | 6/2003 | Chen et al. |

FOREIGN PATENT DOCUMENTS

| | | | |
|---|---|---|---|
| DE | 2 449 865 | | 4/1976 |
| DE | 3 630 603 | | 3/1988 |
| DE | 19615820 | * | 10/1997 |
| EP | 0 219 762 | | 4/1987 |
| EP | 0 250 187 | | 12/1987 |
| EP | 0 259 749 | | 3/1988 |
| EP | 0 381 194 | | 8/1990 |
| EP | 0 200 508 | | 10/1991 |
| EP | 0 452 446 | | 10/1991 |
| EP | 0 526 524 | | 12/1995 |
| EP | 0 781 550 | | 7/1997 |
| EP | 0 781 546 | | 3/2001 |
| EP | 1 103 253 | | 5/2001 |
| EP | 1 391 212 | | 2/2004 |
| JP | 5-41602 | | 6/1993 |
| JP | 5-236885 | | 9/1993 |
| WO | 91/05540 | | 5/1991 |
| WO | 91/06270 | | 5/1991 |
| WO | 92/15289 | | 9/1992 |
| WO | 95/18046 | | 7/1995 |
| WO | 00/10539 | | 3/2000 |
| WO | 00/42992 | | 7/2000 |
| WO | 01/03917 | | 1/2001 |
| WO | 01/07507 | | 2/2001 |
| WO | 01/30288 | | 5/2001 |
| WO | 02/02085 | | 1/2002 |
| WO | 02/066016 | | 8/2002 |
| WO | 02/085119 | | 10/2002 |
| WO | 03/015748 | | 2/2003 |
| WO | 03/026654 | | 4/2003 |
| WO | 03/030883 | | 4/2003 |

OTHER PUBLICATIONS

Y.W. Chien, Novel *Drug Delivery Systems*, New York: Marcel Dekker, Inc., 1992, pp. 171-173.

V.V. Ranade and M.A. Hollinger (ed.): *Drug Delivery Systems*, Florida: CRC Press, Inc., 1996, pp. 62-65.

J. Anderson, Advances in Drug Delivery Systems, 6, pp. 37-38 (1994).

CAPLUS abstract (1986:193234) & JP 61030516.

* cited by examiner

WATER SOLUBLE FILM FOR ORAL ADMINISTRATION WITH INSTANT WETTABILITY

This application is a continuation application of Ser. No. 10/143,962 filed May 14, 2002, now U.S. Pat. No. 6,709,671, which is a continuation application of Ser. No. 09/927,327 filed Aug. 13, 2001, now abandoned, which is a continuation application of Ser. No. 09/630,562 filed Aug. 2, 2000, now U.S. Pat. No. 6,284,264, which is a divisional application of Ser. No. 09/287,181 filed Apr. 6, 1999, now U.S. Pat. No. 6,177,096, which is a continuation application of Ser. No. 08/904,607 filed Aug. 1, 1997, now U.S. Pat. No. 5,948,430.

A composition containing therapeutic agents and/or breath freshening agents for use in the oral cavity is disclosed. The carrier comprises water-soluble polymers in combination with certain ingredients and provides a therapeutic and/or cosmetic effect. The film is coated and dried utilizing existing coating technology and exhibits instant wettability followed by rapid dissolution/disintegration upon administration in the oral cavity.

BACKGROUND OF THE INVENTION

Mucoadhesive dosage forms for application to the oral cavity which are designed to deliver therapeutic and/or cosmetic agents to the oral mucosa are known in the art. U.S. Pat. No. 5,047,244 describes a mucoadhesive carrier allowing the controlled release of a therapeutic agent via the mucosal tissue comprising an anhydrous but hydratable polymer matrix and amorphous fumed silica. An optional water-insoluble film can be added to provide a non-adhering surface. In WO 91/06270, the same authors disclose a trilaminate film suitable for prolonged delivery of an active ingredient in the oral cavity.

In a similar way, U.S. Pat. No. 4,876,092 discloses a sheet-shaped adhesive preparation comprising an adhesive layer containing certain water-soluble and water-insoluble polymers and a water-insoluble carrier which can adhere to the oral mucosa thereby releasing an active agent to the oral cavity. All the devices so far cited are not completely water soluble and will stay in the oral cavity even after the therapeutic goal has been achieved leaving the patient with a certain discomfort in the mouth resulting mainly from the support layer which leaves an insoluble residue in the mouth.

A number of attempts have been made to reduce the adverse feeling in the oral cavity caused by the rigidity and inflexibility of the support layer by introducing soft film supports. EP 0 200 508 B1 and EP 0 381 194 B1 disclose the use of polyethylene films, polyvinyl acetate, ethylene-vinyl acetate copolymers, metal foils, laminates of cloth or paper and a plastic film, and similar materials as soft film supports, whereby synthetic resins like polyethylene, vinyl acetate homopolymers, and ethylene-vinyl acetate are the preferred materials. In a similar way, CA 1 263 312 discloses the use of polyolefines such as polyethylene, polypropylene, polyesters, PVC, and non-woven fabrics as soft support materials.

However, these devices still leave the patient with a considerable amount of residue from the water-insoluble support film thereby still causing a feeling of discomfort. The obvious solution to overcome this problem was to develop mucoadhesive films which completely disintegrate, or even completely dissolve in the saliva. Fuchs and Hilmann (DE 24 49 865.5) prepared homogeneous, water-soluble films intended for buccal administration of hormones. They proposed the use of water-soluble cellulose-derivatives, like hydroxyethyl cellulose, hydroxypropyl cellulose, or methyl hydroxypropyl cellulose, as film forming agents.

Both DE 36 30 603 and BP 0 219 762 disclose the use of swellable polymers such as gelatins or corn starch as film forming agents, which upon application to the oral cavity, slowly disintegrate, thereby releasing an active ingredient incorporated in the film. The same polymers can also b used to prepare films which are intended for dental cleansing, as described in EP 0 452 446 B1.

These preparations still create an adverse feeling in the mouth which is mainly caused by their initial rigidity and delayed softening. Thus, there has still been a demand for a composition for use in the oral cavity which meets the requirement of providing a pleasant feeling in the mouth. The present invention discloses methods and compositions that are capable of avoiding an adverse feeling by providing the film which is intended for application to the oral mucosa with instant wettability, while achieving adequate tensile strength in the free film to allow for easy coating, converting, and packaging of a consumer-friendly product.

DESCRIPTION OF THE INVENTION

The present invention contemplates a rapidly dissolving film which can be adhered to the oral cavity thereby releasing a pharmaceutically or cosmetically active agent, said film comprising water-soluble polymers, one or more polyalcohols, and one or more pharmaceutically or cosmetically active ingredients. Optionally, the formulation may contain a combination of certain plasticizers or surfactants, colorants, sweetening agents, flavors, flavor enhancers, or other excipients commonly used to modify the taste of formulations intended for application to the oral cavity. The resulting film is characterized by an instant wettability which causes the film to soften immediately after application to the mucosal tissue thus preventing the patient from experiencing any prolonged adverse feeling in the mouth, and a tensile strength suitable for normal coating, cutting, slitting, and packaging operations.

The mucoadhesive film of the present invention contains as essential components a water-soluble polymer or a combination of water-soluble polymers, one or more plasticizers or surfactants, one or more polyalcohols, and a pharmaceutically or cosmetically active ingredient.

The polymers used for the mucoadhesive film include polymers which are hydrophilic and/or water-dispersible. Preferred polymers are water-soluble cellulose-derivatives. Hydroxypropylmethyl cellulose, hydroxyethyl cellulose, or hydroxypropyl cellulose, either alone, or mixtures thereof, are particularly preferred. Other optional polymers, without limiting the invention, include polyvinyl pyrrolidone, carboxymethyl cellulose, polyvinyl alcohol, sodium alginate, polyethylene glycol, natural gums like xanthan gum, tragacantha, guar gum, acacia gum, arabic gum, water-dispersible polyacrylates like polyacrylic acid, methylmethacrylate copolymer, carboxyvinyl copolymers. The concentration of the water-soluble polymer in the final film can vary between 20 and 75% (w/w), preferably between 50 and 75% (w/w).

The surfactants used for the mucoadhesive film may be one or more nonionic surfactants. When a combination of surfactants is used, the first component may be a polyoxyethylene sorbitan fatty acid ester or a α-hydro-ω-hydroxypoly(oxyethylene)poly(oxypropylene)poly(oxyethylene) block copolymer, while the second component may be a polyoxyethylene alkyl ether or a polyoxyethylene castor oil derivative. Preferably, the HLB value of the polyoxyethylene sorbitan fatty acid ester should be between 10 and 20, whereby a range of 13 to 17 is particularly pr ferred. The α-hydro-ω-hydroxypoly(oxyethylene)poly(oxypropylene) poly(oxyethylene) block copolymer should contain at least 35 oxypropylene-units, preferably not less than 50 oxypropylene-units.

The polyoxyethylene alkyl ether should have an HLB value between 10 and 21, whereby an HLB value of not less than 15 is preferred. The polyoxyethylene castor oil derivative has to have an HLB value of 14-16.

In order to achieve the desired instant wettability, the ratio between the first and second component of the binary surfactant mixture should be kept within 1:10 and 1:1, more preferably between 1:5 and 1:3.

The total concentration of surfactants in the final film depends on the properties of the other ingredients, but usually has to stay between 0.1 and 5% (w/w).

The polyalcohol is used to achieve the desired level of softness of the film. Examples of polyalcohols include glycerol, polyethylene glycol, propylene glycol, glycerol monoesters with fatty acids or other pharmaceutically used polyalcohols. The concentration of the polyalcohol in the dry film usually ranges between 0.1 and 5% (w/w).

The film is well suited for the delivery of a wide range of pharmaceutically active ingredients via the mucous membranes of a patient, particularly the buccal mucosa. Therapeutic agents which exhibit absorption problems due to solubility limitations, degradation in the gastro-intestinal tract, or extensive metabolism, are particularly well suited. Without limiting the invention, examples of the therapeutic agents include hypnotics, sedatives, antiepileptics, awakening agents, psychoneurotropic agents, neuromuscular blocking agents, antispasmodic agents, antihistaminics, antiallergics, cardiotonics, antiarrhythmics, diuretics, hypotensives, vasopressors, antitussive expectorants, thyroid hormones, sexual hormones, antidiabetics, antitumor agents, antibiotics and chemotherapeutics, and narcotics.

The amount of drug to be incorporated into the film depends on the kind of drug and is usually between 0.01 and 20% (w/w), but it can be higher if necessary to achieve the desired effect.

Cosmetically active agents may include breath freshening compounds like menthol, other flavors or fragrances commonly used for oral hygiene, and/or actives used for dental and/or oral cleansing like quarternary ammonium bases. The effect of flavors may be enhanced using flavor enhancers like tartaric acid, citric acid, vanillin, or the like. Colorants which may optionally be mixed in the film must be safe in terms of toxicity and should be accepted by the Food And Drug Administration for use in cosmetics.

The mucoadhesive film according to the present invention can be prepared as follows: The polyalcohol, surfactants, plasticizers, and possible other ingredients except the water-soluble or water-dispersible polymer(s) are dissolved in a sufficient amount of a solvent which is compatible with them. Examples of compatible solvents include water, alcohols or mixtures thereof. After a clear solution has been formed, the water-dispersible polymer or mixture of water-dispersible polymers in slowly added with stirring, and heat if necessary, until a clear and homogeneous solution has been formed, followed by the addition of active ingredients and flavors. The solution is coated onto a suitable carrier material and dried to form a film. The carrier material must have a surface tension which allows the polymer solution to spread evenly across the intended coating width without soaking in to form a destructive bond between the two. Examples of suitable materials include non-siliconized polyethylene terephthalate film, non-siliconized kraft paper, polyethylene-impregnated kraft paper, or non-siliconized polyethylene film.

The coating of the solution onto the carrier material can be performed using any conventional coating equipment. A more preferred-coating technique would involve a knife-over-roll coating head.

The thickness of the resulting film depends on the concentration of solids in the coating solution and on the gap of the coating head and can vary between 5 and 200 μm. Drying of the film is carried out in a high-temperature air-bath using a drying oven, drying tunnel, vacuum drier, or any other suitable drying equipment, which does not adversely affect the active ingredient(s) or flavor of the film. In order to reliably avoid an adverse feeling in the mouth, a dry film thickness of 70 μm should not be exceeded.

For better ease of use, the dry film can be cut into pieces of suitable size and shape and packed into a suitable container.

The invention will now be explained more specifically with reference to the following examples, which are given for illustration of this invention and are not intended to be limiting thereof.

EXAMPLE 1

15 g of sorbitol, 6 g of glycerol, 0.5 g of polysorbate 80 (Tween 80), 2 g of Brij 35, 25 g of lemon mint flavor, 3 g of aspartame, 15 g of 1-menthol, and 3 g of citric acid are stirred at 60° C. in a mixture of 250 g water and 250 g ethanol until a clear solution has been formed. To the solution, 30 g of hydroxypropylmethyl cellulose are added slowly under stirring until a clear and homogeneous solution has been formed. The resulting solution is allowed to cool to room temperature and coated onto a suitable carrier material, for example non-siliconized, polyethylene-coated kraft paper using conventional coating/drying equipment. Coating gap and web speed have to be adjustable to achieve a dry film thickness between 20 and 50 μm. The drying temperature depends on the length of the drying oven and the web speed and has to be adjusted to remove the solvents completely, or almost completely, from the film. The resulting film is peeled off the carrier web and cut into pieces of a shape and size suitable for the intended use.

EXAMPLE 2

3 g sorbitol, 1.5 g Kollidon 30 (supplier: BASF), 5 g glycerol, 5 g propylene glycol, 5 g polyethylene glycol, 4 g polysorbate 80 (Tween 80), 8 g Brij 35, 12 g peppermint flavor, and 0.8 g aspartame are dissolved in a mixture containing 400 g water and 400 g ethanol at 60° C. under stirring. To the clear solution, 28 g hydroxypropylmethyl cellulose are added slowly under stirring. After the polymer is completely dissolved, the solution is cooled to room temperature and coated onto a suitable carrier web using the coating and drying conditions as described in the previous example. The dry film is again out into pieces of suitable size and shape.

EXAMPLE 3

15 g sorbitol, 22.5 g glycerol, 2.5 g propylene glycol, 2.5 g Brij 35, 2.5 g poloxamer 407, 3.5 g Cremophor RH 40, 9 g herb mint flavor, and 0.5 g aspartame are dissolved under stirring at 60° C. in a mixture containing 250 g water a 250 g ethanol. To the clear solution, 75 g hydroxypropyl cellulose are added slowly under continuous stirring. The clear solution is again coated and dried under the conditions as described in EXAMPLE 1 and the dry film is cut into pieces of a shape and size suitable for the intended use.

EXAMPLE 4

3.6 g Tween 80, 3.6 g glycerol, 39 g menthol, and 171 g Kollidon 30 are dissolved in a solution of 600 ml water and 2800 ml ethanol at ambient temperature with stirring. 247.5 g hydroxypropylmethyl cellulose is then added slowly and portionwise at 50-55° C. and stirred until completely dissolved. The mixture is then allowed to cool and added in succession are 90 g lemon mint flavor followed by a solution/suspension of 27.13 g aspartame, 18 g citric acid, and 0.17 g FD&C yellow #5 in 120 ml water with stirring. The clear solution is coated and dried under the conditions as described in EXAMPLE and the dry film in cut into pieces of a shape and size suitable for the intended use.

EXAMPLE 5

4 g Kollidon 30 are dissolved in a solution of 720 ml water and 2660 ml ethanol at ambient temperature with stirring. 220.5 g hydroxypropylmethyl cellulose is then added at 55-60° C. and stirred vigorously until clear and homogeneous. The mixture in then allowed to cool and added in succession are 78.75 g flavor followed by a mixture of 28.8 g nicotine salicylate and 31.5 g caramel liquid in 120 ml water with stirring. The clear, tan-colored solution is coated an dried under the conditions as described in EXAMPLE 1 and the dry film is cut into pieces of a shape and size suitable for the intended use so as to deliver a nicotine dose between 1-2 mg per piece.

The invention claimed is:

1. A composition applicable to the oral cavity, for releasing active substances in the oral cavity, wherein the composition comprises polyvinyl pyrrolidone and hydroxypropylmethyl cellulose, a nicotine salt, and, a water-dispersible methyl methacrylate copolymer,
    wherein said composition exhibits instant wettability which causes the composition to soften immediately after application to the oral mucosa, followed by rapid dissolution or disintegration of the composition, and said composition is a dry film that is orally applicable and that has a thickness of not more than 70 µm.

2. The composition according to claim 1, wherein the thickness of said film is between 5 and 70 µm.

3. The composition according to claim 1, further comprising at least one water-soluble or water-dispersible polymer selected from the group consisting of a water-soluble cellulose derivative, polyvinyl alcohol, sodium alginate, polyethylene glycol, a natural gum, water-dispersible polyacrylate, and a mixture of the aforementioned polymers.

4. The composition according to claim 1, wherein the concentration of the polyvinyl pyrrolidone and hydroxypropylmethyl cellulose is between 20 and 75%-wt.

5. The composition according to claim 1, further comprising at least one polyalcohol.

6. The composition according to claim 5, wherein the proportion of the polyalcohol is 0.1 to 5%-wt. of the dry composition.

7. The composition according to claim 1, further comprising at least one surfactant, the total concentration of surfactant(s) being in the range of 0.1 to 5%-wt.

8. The composition according to claim 1, wherein the amount of nicotine salt is between 0.01 and 20%-wt.

9. The composition according to claim 1, further comprising one or more members selected from the group consisting of a flavor, a flavor enhancer and a fragrance.

10. The composition according to claim 1, further comprising a cosmetically active ingredient that is selected from the group consisting of a breath freshening compound, a flavor used for oral hygiene, a fragrance used for oral hygiene, an active agent used for oral cleansing, and an active agent used for dental cleansing.

11. The composition according to claim 1, wherein the nicotine salt is nicotine salicylate.

12. The composition according to claim 3, wherein the water-soluble cellulose derivative is hydroxyethyl cellulose or hydroxypropyl cellulose; the natural gum is xanthan gum, tragacantha, guar gum, acacia gum or arabic gum; and the water-dispersible polyacrylate is polyacrylic acid.

13. The composition according to claim 4, wherein the concentration of the polyvinyl pyrrolidone and hydroxypropylmethyl cellulose is between 50 and 75%-wt.

14. The composition according to claim 5, wherein the polyalcohol is selected from the group consisting of glycerol, polyethylene glycol, propylene glycol, and a glycerol monoester with fatty acids.

15. The composition according to claim 9, wherein the one or more members is selected from the group consisting of menthol, lemon mint flavor, peppermint flavor, herb mint flavor, aspartame and caramel.

16. The composition according to claim 1, further comprising caramel.

17. The composition according to claim 16, wherein said nicotine salt is nicotine salicylate.

18. The composition according to claim 1, wherein the composition further comprises polyacrylic acid.

19. The composition according to claim 3, wherein the water-soluble cellulose derivative is carboxymethyl cellulose.

* * * * *